United States Patent
Bates

(10) Patent No.: US 7,807,468 B2
(45) Date of Patent: Oct. 5, 2010

(54) METHODS OF MARKING AND TESTING PHARMACEUTICAL PRODUCTS

(76) Inventor: Lynn S. Bates, c/o Alteca Ltd., 731 McCall Rd., Manhattan, KS (US) 66502-5037

( * ) Notice: Subject to any disclaimer, the term of this patent is extended or adjusted under 35 U.S.C. 154(b) by 1352 days.

(21) Appl. No.: 11/233,240

(22) Filed: Sep. 21, 2005

(65) Prior Publication Data

US 2006/0018832 A1 Jan. 26, 2006

Related U.S. Application Data

(63) Continuation-in-part of application No. 10/897,781, filed on Jul. 21, 2004.

(51) Int. Cl.
*A61K 49/00* (2006.01)
(52) U.S. Cl. .................. 436/56; 436/63; 436/172; 435/7.1; 424/9.1; 424/457
(58) Field of Classification Search .............. 436/56, 436/63, 172; 435/7.1; 424/9.1, 457
See application file for complete search history.

(56) References Cited

U.S. PATENT DOCUMENTS

| | | | |
|---|---|---|---|
| 6,068,981 A * | 5/2000 | Rittenburg et al. | 435/7.1 |
| 6,180,354 B1 * | 1/2001 | Singh et al. | 435/7.1 |
| 6,461,607 B1 * | 10/2002 | Farmer | 424/93.45 |
| 6,649,414 B1 * | 11/2003 | Chandler et al. | 436/63 |

OTHER PUBLICATIONS

Wolf, Lauren, "Newscripts: Probiotic Allergy Relief, Fighting Crime with Pollen," CEN-Online.org, p. 88, Aug. 18, 2008.
Chamot, Handbook of Chemical Microscopy, 2nd ed. 1954, pp. 431-443, vol. I, John Wiley & Sons, Inc.
Mullin, Rick, "Recalibrating the Clinic," C&EN, Feb. 28, 2005, pp. 29-39.
Dyer, Nicole, "Stealth Tags That Foil Counterfeiters," Popular Science, Jul. 2005, p. 34.
See Also, references cited in Applicant's copending U.S. Appl. No. 10/897,781, filed Jul. 21, 2004.

* cited by examiner

Primary Examiner—Jill Warden
Assistant Examiner—Dwan A Gerido
(74) Attorney, Agent, or Firm—Jeffrey L. Thompson; Thompson & Thompson, P.A.

(57) ABSTRACT

Methods of marking pharmaceutical products for use in clinical trials and for determining the origin or authenticity of the marked products are provided that use a variety of natural materials as markers. The natural materials have unique genetically controlled micromorphological structures that can be identified using enhanced visualization techniques. For example, cellulosic plant materials, sporopollenin and diatoms can be used as the natural materials. The natural materials are added to pharmaceutical products at sufficiently low levels so as not to have any significant effect on the products other than serving as markers. Dyes and reactants can be added to the natural materials to provide secondary markers. The markers can be identified in stool samples collected during clinical trials to prove that a particular pharmaceutical product has been ingested by a test subject.

7 Claims, 3 Drawing Sheets

METHODS OF MARKING AND TESTING PHARMACEUTICAL PRODUCTS

RELATED APPLICATIONS

This application is a continuation-in-part of U.S. patent application Ser. No. 10/897,781 filed on Jul. 21, 2004, the content of which is incorporated herein by reference.

FIELD OF THE INVENTION

The present invention relates to the marking of products to establish their identity and source. In particular, the present invention relates to the use of various natural materials having genetically controlled micromorphological structures as markers for the identification of pharmaceutical products, and using such markers during pharmaceutical testing to prove that the tested product has been ingested by a person.

BACKGROUND OF THE INVENTION

Clinical trials are used in the pharmaceutical industry to study human volunteers to answer specific health questions. Clinical trials are conducted in phases, with each phase having a different purpose. Phase I trials are used to test experimental drugs or treatments in a small group of people (20-80) to evaluate its safety, determine a safe dosage range, and identify side effects. Phase II trials are used to give the experimental drug or treatment to a larger group of people (100-300) to see if it is effective and to further evaluate its safety. Phase III trials are used to give the experimental drug or treatment to large groups of people (1,000-3,000) to confirm its effectiveness, monitor side effects, compare it to commonly used treatments, and collect information that will allow the experimental drug or treatment to be used safely.

Clinical trials are conducted according to a specific protocol or study plan developed for each trial. The protocol is designed to increase the reliability of the study, as well as to safeguard the health of the participants and to answer specific research questions. The protocol typically describes what types of people may participate in the trial, the schedule of tests, procedures, medications, and dosages; and the length of the study. Participants following a protocol are typically seen regularly by the research staff to monitor their health and to determine the safety and effectiveness of their treatment.

During clinical trials, it is often difficult to know with certainty whether someone is taking a prescribed drug. Feces monitoring is done sometimes to make sure people are eating healthy. However, in most cases such feces monitoring does not provide conclusive proof that a particular drug has been ingested by the test subject. Adding a marker to the drug being tested has not been a viable option because of a concern for the safety of the test subject, as well as the potential interaction with the drug being tested and the effect on the clinical trial.

Markers are commonly used in the processed food industry to identify small quantities of returned food items that may or may not be in their original packaging, which may or may not be correctly identified by the person returning the item(s), or for any other of many reasons. Specific markers that can trace the identity of a food back to its original processing location are sometimes required by food manufacturers.

Markers in the food industry need to trace a wide range of processed foods, some of which cannot be readily adapted to having materials added to them. In some cases, sub-cellular markers may have to be used to provide identity. In others, cellular or multi-cellular materials may be used. Many spices and preservatives can be markers themselves, as well as in conjunction with morphological markers to provide additional specificity for product identifications. Sometimes a completed food item has components from several sources. Markers of different kinds are needed to identify the manufacturers of buns and meat patties that become part of a completed food product or system. The similarity of baked buns, for example, makes it critical for a supplier of buns to be able to identify their products from those of another supplier of buns used in the same restaurant or outlet. It is particularly critical when liability must be determined for foreign material reportedly found in a bun where two suppliers are used at the same location. In addition, the markers used in buns cannot confound those used in meats or condiments, and so forth.

SUMMARY OF THE INVENTION

An object of the present invention is to provide a method of marking pharmaceutical products to solve the problems with the prior art discussed above.

It is a further object of the present invention to provide a method of marking drugs used in clinical trials, which can be used to prove a particular drug has been ingested by a person.

It is a further object of the present invention to provide a method of marking pharmaceutical products that uses natural cellulosic material or other natural polymers or materials that are non-allergenic, that can be matched to the characteristics and functional properties of the pharmaceutical product, and that are resistant to visible changes induced by mechanical, physical or chemical processing variables during manufacturing and digestion of the pharmaceutical product.

It is a further object of the present invention to provide a method of marking pharmaceutical products that offers a large number of distinct markers that can be identified rapidly using enhanced visualization techniques.

To achieve these and other objects of the present invention, the Applicant has developed methods of marking pharmaceutical products for use in clinical trials and for determining the origin or authenticity of the marked products using a variety of natural materials as markers. The natural materials have unique genetically controlled micromorphological structures that can be identified using enhanced visualization techniques. For example, cellulosic plant materials, sporopollenin and diatoms can be used as the natural materials. The natural materials are added to pharmaceutical products at sufficiently low levels so as not to have any significant effect on the products other than serving as markers. Dyes and reactants, particularly chromophoric reactants, can be added to the natural materials to provide secondary markers. The secondary markers can be vacuum infused into hollow interior spaces of the natural materials, or placed in surface voids of the natural materials to remain secured in the marker structures until examined. Sub-cellular particles, such as starch granules, and heat sensitive molecules, such as enzymes, can also be used to provide a molecular thermometer for the markers. The markers can be identified in stool samples collected during clinical trials to prove that a particular pharmaceutical product has been ingested by a test subject.

According to a broad aspect of the present invention, a method of marking pharmaceutical products is provided, comprising the steps of: selecting a natural material having a unique genetically controlled micromorphological structure that can be identified using an enhanced visualization technique; and adding said natural material to a pharmaceutical product unrelated to said natural material at a sufficiently low level so as not to have any significant effect on the product other than to serve as a marker for the product.

According to another broad aspect of the present invention, a method of proving ingestion of a pharmaceutical product by a person participating in a clinical trial is provided, comprising the steps of: obtaining a stool sample from the person after a pharmaceutical product is allegedly ingested; and determining by use of enhanced visualization whether the stool sample contains a particular natural material having a unique genetically controlled micromorphological structure indicative of a presence of the pharmaceutical product.

According to another broad aspect of the present invention, a method of providing a plurality of different markers for pharmaceutical products is provided, comprising the steps of: providing at least one natural material having a unique genetically controlled micromorphological structure; providing at least one secondary marker selected from the group consisting of dyes and reactants; and making a plurality of different combinations of said at least one natural material and said at least one secondary marker to provide a plurality of different markers for pharmaceutical products.

Numerous other objects of the present invention will be apparent to those skilled in this art from the following description wherein there is shown and described exemplary embodiments of the present invention. As will be realized, the invention is capable of other different embodiments, and its several details are capable of modification in various obvious aspects without departing from the invention. Accordingly, the drawings and description should be regarded as illustrative in nature and not restrictive.

BRIEF DESCRIPTION OF THE DRAWINGS

The present invention will become more clearly appreciated as the disclosure of the invention is made with reference to the accompanying drawings. In the drawings.

DETAILED DESCRIPTION OF THE INVENTION

Figure 1:
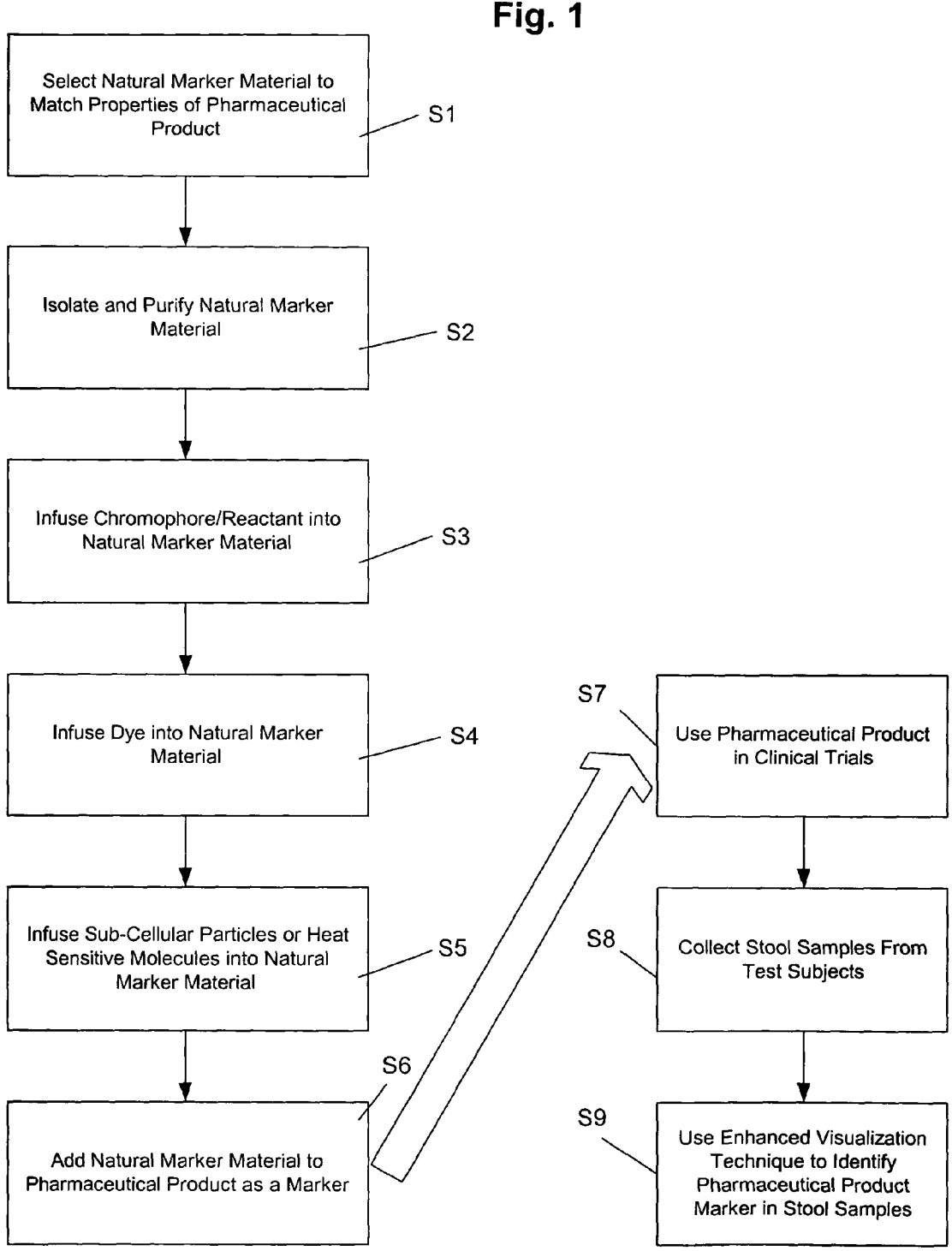
FIG. 1 is a flow chart of a process for marking pharmaceutical products using natural marker materials according to the present invention.

A detailed description of exemplary embodiments of the present invention is provided herein. It is, however, to be understood that the disclosed embodiments are merely illustrative of the invention, which may be embodied in various forms. Therefore, specific structural and functional details disclosed herein are not to be interpreted as limiting, but merely as a basis for the claims and as a representative basis for teaching one skilled in the art to employ the process of the present invention.

Overview

The wide range of diverse life forms on Earth produce an equally wide range of unique cells and sub-cellular particles that can be harvested and processed. These cells and particles are genetically controlled and thus remain the same from year to year in each new generation of a particular species. Many of these cells and particles are also resistant to any significant modifications caused by the physical forces and chemical changes common to pharmaceutical manufacturing. Thus, there are many cells and particles available to be used as unique identifying tags or markers for the branding or marking of pharmaceutical products and various other manmade products. Most of these available marker materials are fiber or non-digestible materials.

The first type of markers are those materials that are environmentally stable, resistant to processing, Generally Recognized As Safe ("GRAS"), and common to the type of pharmaceutical product being marked. For example, a very specific cereal cell type, a cellulosic fiber fraction, for example, can be isolated and used to mark all the pharmaceutical products from a particular manufacturer. The unique specificity of these markers would allow them to be used at very low levels in the pharmaceutical product.

The second type of markers are those materials that fit the above criteria but are specific fibrous cell types from non-traditional bakery food ingredients. These markers would make the identification more specific for a particular pharmaceutical product, but might not be able to be included in all the pharmaceutical products from a particular manufacturer. The presence of a cellular and/or a secondary sub-cellular fraction would offer additional identification probabilities for pharmaceutical products. If used at sufficiently low levels, the marker source will not have any effect on the pharmaceutical product, other than to serve as a marker for the product.

In many cases, the cells and particles of interests are by-products or sub-products of food processing and have become feed ingredients. These are available in large quantities but may have one or more characteristics that cause them to be removed. For example, they may be highly fibrous, tough, hard, colored or undesirable for whatever other reason and are removed to enhance the value of the food. However, many of these materials can be further processed to make isolates that are unique and GRAS. In other cases, the unique tag or marker may be found in a wild relative of one of our common crop plants that is GRAS but perhaps lacks the desirable characteristics of its domestic counterpart for agronomic or processing reasons. These too can be grown, harvested and the unique marker(s) processed and concentrated for tracing pharmaceutical products. Unique markers may also be found in non-traditional portions of a food source, such as pollen, that can be processed to create totally unique markers. Of course the pollen must be purified to remove surface antigens and allergens before it can be used as a marker for pharmaceutical products.

Natural Marker Materials

The present invention uses the natural cellular characteristics of certain materials that have unique genetically controlled micromorphological structures that can be identified rapidly in several ways with the aid of a microscope or other enhanced visualization methods. The natural materials are non-allergenic and can be selected to match the characteristics and functional properties of a particular pharmaceutical product being marked. These can be subsequently built upon or in to produce added specificity to the natural genetic micromorphological marker. The natural marker materials will be selected to be resistant to visible changes induced by mechanical, physical or chemical processing variables during manufacturing of the marked product. The step of selecting a natural marker material to match the properties of a pharmaceutical product in which it will be used is shown as step S1 in FIG. 1.

The natural marker materials can be obtained from a variety of sources, including natural cellulosic plant materials, sporopollenin, and diatoms. In one embodiment, the natural marker material is cellulosic plant material comprising hollow plant fibers. For example, the hollow plant fibers can be sycamore seed fibers, oat trichomes, milkweed pods, capok, alfalfa trichomes, and so forth. Other sources of plant fibers, such as weed seeds, leaves and cockle burrs, can also be used. Plant appendages, such as plant hairs and the like, provide particularly good sources of genetically controlled micromorphological structures that can be identified rapidly under a microscope.

The natural cellulosic plant material will preferably have either hollow interior spaces, as in the hollow plant fibers described above, or surface voids or pits (collectively referred to herein as "surface voids"). As explained below, secondary markers can be placed in the hollow interior spaces and surface voids of the natural cellulosic material to create specificity and enhanced visibility. The natural marker material is then added to the pharmaceutical product, as indicated in step S6 in FIG. 1, at sufficiently low levels so as not to have any significant effect on the product other than to serve as a marker for the product.

The purification of such a wide range of materials is not possible with a single type of method. Plant cell isolation has no general method. Each type of cell requires a different method. Leaf cells, pollen, stem cells, and seed tissues will all be different. The methods to isolate these fractions are available within the confines of known food and/or drug processing techniques. Once the desired plant material is isolated, it may be necessary to grind the plant fibers to obtain the desired particulate size for the markers. The step of isolating and purifying the natural marker material is shown as step S2 in FIG. 1.

Pollen and allergenic particles can also be used as markers and are of particular interest because of their tough stable exine layer and their unique structures. The pollen can be cleaned of the surface antigens and the active enzymes in the interior leaving only the exine for identification purposes. Only the exine will generally be used for the marker material because it is easily identified and formed of sporopollenin, which is a relatively inert polymer that is environmentally stable and thus not modified by most food or drug processing. The specific pollen source will determine the exact purification technique. The purification process will involve a combination of enzymatic, acidic and/or alkaline hydrolysis, flotation, decantation, centrifugation, drying and agglomerated particle reduction.

Diatoms can also be used as the natural materials for the markers of the present invention because they have silicified skeletons with a unique genetically controlled micromorphological structure that can be identified easily under a microscope. Although diatoms are normally not suitable for marking food products because they tend to impart an undesirable grittiness to the food that can be felt by the mouth, such concerns will not generally be a problem with pharmaceutical products. The silicified skeletons of the diatoms are the product of the genetics of a particular organism and thus a parallel situation to the cellulosic plant material and sporopollenin materials described above.

Secondary Markers

The natural marker materials described above can be modified using dyes and/or reactants and particularly chromophoric reactants to produce a secondary marker effect. The secondary markers will be added to the unique structures of the natural marker materials to enhance the visibility of the markers, as well as to increase the number of possible marker combinations, thereby creating specificity where multiple markers are required. The step of adding reactants into the natural marker material is shown as step S3 in FIG. 1, and the step of infusing dyes or other colorants into the natural marker material is shown as step S4.

The secondary marker can be in the form of one or more reactants, particularly chromophoric reactants, that are added to the natural cellulosic markers. These are compounds that will react with specific reagents to produce color many times more intense than that of dyes or other colorants. An example of the use of a chromophore is the use of iron salts. The presence of iron can be detected readily by converting it to an indigo blue. When the indigo blue is not in a cell where natural iron would be found, and the blue is in a specific micromorphological marker, the product can be clearly confirmed to be the marker. Copper is another example of a metallic ion that is commonly ingested and that can be determined to be located in a particular structure rather than distributed throughout the product matrix.

The secondary marker can also be in the form of a dye or other colored compound added to the natural cellulosic markers. A dye molecule, either a natural dye like an anthocyanin or a synthetic dye like an FDA Red 40, entrapped in the specific structure of a micromorphological marker adds to the specificity of the marker and enhances its visual characteristics. The more specific layers that can be added to a natural genetic micromorphological marker increases the number of related similar products that can be marked. The dye compounds can also provide a molecular signature should one require more than a rapid subjective examination.

Figure 2:
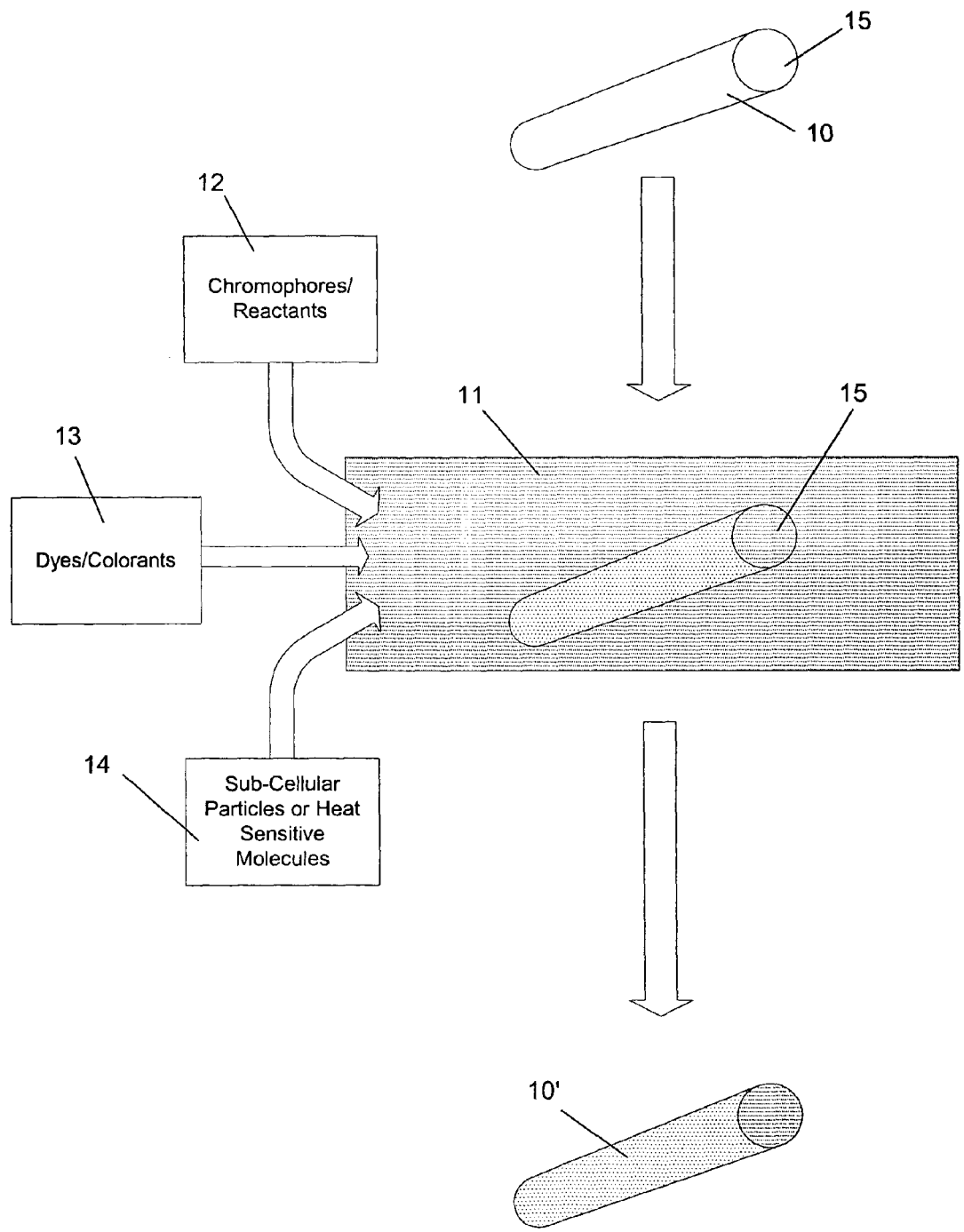
FIG. 2 is a diagram showing the process for making markers for pharmaceutical products using natural cellulosic plant material having hollow fibers according to the present invention.

As explained above, many of the natural cellulosic markers available for use in pharmaceutical products according to the present invention are hollow. The secondary dyes and reactants can be vacuum infused into the hollow interior spaces of the natural cellulosic markers where they are protected from subsequent processing. As depicted in FIG. 2, the hollow cellulosic material 10 is placed in a vacuum chamber 11 with the secondary marker materials 12, 13 and sub-cellular particles or heat sensitive molecules 14 (explained below) for a sufficient time and under a sufficient vacuum that the secondary marker materials 12, 13 and sub-cellular particles or heat sensitive molecules 14 infuse into the hollow interior spaces 15 of the cellulosic material 10. The infused cellulosic material 10' is then ready for use as a marker in a pharmaceutical product.

In other cases, the secondary characteristics provided by the dyes and reactants can be enrobed in or absorbed into carriers that can fill surface voids and pits and thereby remain secured in the marker structures until examined.

Molecular Thermometers

Sub-cellular particles or heat sensitive molecules 14 (FIG. 2) can be added to the natural micromorphological markers to provide a molecular thermometer for the marker. This is shown as step S5 in FIG. 1. For example, starch granules or enzymes can be vacuum infused into the hollow interior spaces or attached to the surfaces of the natural cellulosic markers. Starch granules that gelatinize at a temperature just below a process temperature can be used to provide an internal molecular thermometer to a cooking process that must reach a minimum temperature. Enzyme systems work in a similar way, have narrow ranges of denaturation (the point where they lose their activity), and can serve as molecular thermometers around a particular cook point temperature.

Both of these types of markers and other related cellular constituents can be selected to provide process control markers. Intact starch and its gelatinization can be observed with both bright field and polarized light microscopy. When they are inside a hollow marker or affixed to the marker surfaces, they add a temperature monitoring function to the marker.

Enzymatic markers inside the hollow natural markers are best found by incubating a small sample with the visualization reagent in a depression slide or small dish. The colored reaction products formed can be used to confirm the cook temperature depending on the denaturation or activity of the enzyme in a limited time period. The location of the enzyme activity within the hollow interior spaces of the natural cellular marker would confirm the marked product. Enzymes are very specific in their reactivity which adds considerable additional specificity to the markers and to the temperature monitoring aspect of the markers. The enzyme detection solutions used are preferably not present in any form in the pharmaceutical product so that no confounding of results will occur. The markers would be colorless and would not be visible until incubated in a drop of the enzyme test reagent.

Using a natural hollow micro-fiber carrier system is particularly useful for enzyme systems used as fixed point molecular thermometers. In pharmaceutical products, they could be used to monitor the processing temperatures during manufacture. An enzyme system or an enzyme substrate (reactant) could also be used to monitor the environments in which a pharmaceutical product had been submitted over a time frame that would include shipping, warehousing, merchandising, and so forth.

Use of Markers in Clinical Trials

The present invention uses the unique genetically controlled micromorphological structures found in living organisms as materials for marking, tagging, or tracing (collectively referred to herein as "marking") pharmaceutical products, and for proving the ingestion of pharmaceutical products during clinical trials. These unique micromorphological markers can subsequently be found by rapid visual examinations of the marked products without costly or lengthy analyses. Identification of a marker, tag or trace (collectively referred to herein as a "marker") is a simple "presence or absence" determination. It requires no quantifying.

Markers for pharmaceutical products according to the present invention are selected from natural materials having unique genetically controlled micromorphological structures that can be identified using enhanced visualization techniques. The selected marker(s) is added to the pharmaceutical products during manufacturing of the products, as indicated in step S6 in FIG. 1, and is kept at a sufficiently low level so as not to have any significant effect on the product other than to serve as a marker for the product.

The pharmaceutical product is then used during a clinical trial according to an established protocol, as indicated in step S7. During the clinical trial, the people ("test subjects") who are supposed to ingest the pharmaceutical product will collect their stool samples at predetermined times (e.g., within 1-3 days after ingestion of the drug) using known sampling techniques, as indicated in step S8. The stool samples are then analyzed using enhanced visual examination equipment, such as a microscope, to identify the pharmaceutical product marker in the stool sample, as indicated in step S9. If the marker is identified in the stool sample, it can be conclusively proven that the test subject had ingested the pharmaceutical product, thereby increasing the reliability of the test results. The results of the clinical trial will therefore be less likely to be affected by incorrect reporting by test subjects that a particular pharmaceutical product had been ingested, when in fact such product had not been ingested.

Sample Preparation and Detection Techniques

Rapid microscopic examinations depend on minimal sample preparation and ease of observations. These are subjective methods that are "YES-NO" types of tests. Some sample preparation can enhance the examinations. For example, the examination of a natural cellulosic tubular marker in a matrix containing starch can be enhanced by gelatinizing the starches, thereby allowing rapid evaluations and eliminating any confounding of the observations by the background polarized light from the starch. Gelatinizing the starch will destroy its polarized light interference with the natural cellulosic markers during an examination. This can be accomplished by heating a small amount of a marked product on a slide in a mounting medium containing chloral hydrate. Similarly, a sample of the product could be wetted with strong alkali and heated on a slide to gelatinize the starch. A third method of gelatinization would be heating the wetted product on a slide in a steam bath or autoclave to completely gelatinize the starch. Larger samples can be produced when destructive testing is permitted. These can be autoclaved or heated in alkali in a beaker followed by sampling for microscopic examinations.

Clearinghouse for Different Marker Combinations

The natural marker materials and secondary markers described above can be used in various combinations to provide several different markers for pharmaceutical products. This will allow different markers to be used to identify different pharmaceutical manufacturers or suppliers. It will also allow different markers to be used to identify different lots from the same manufacturer or supplier.

Figure 3:
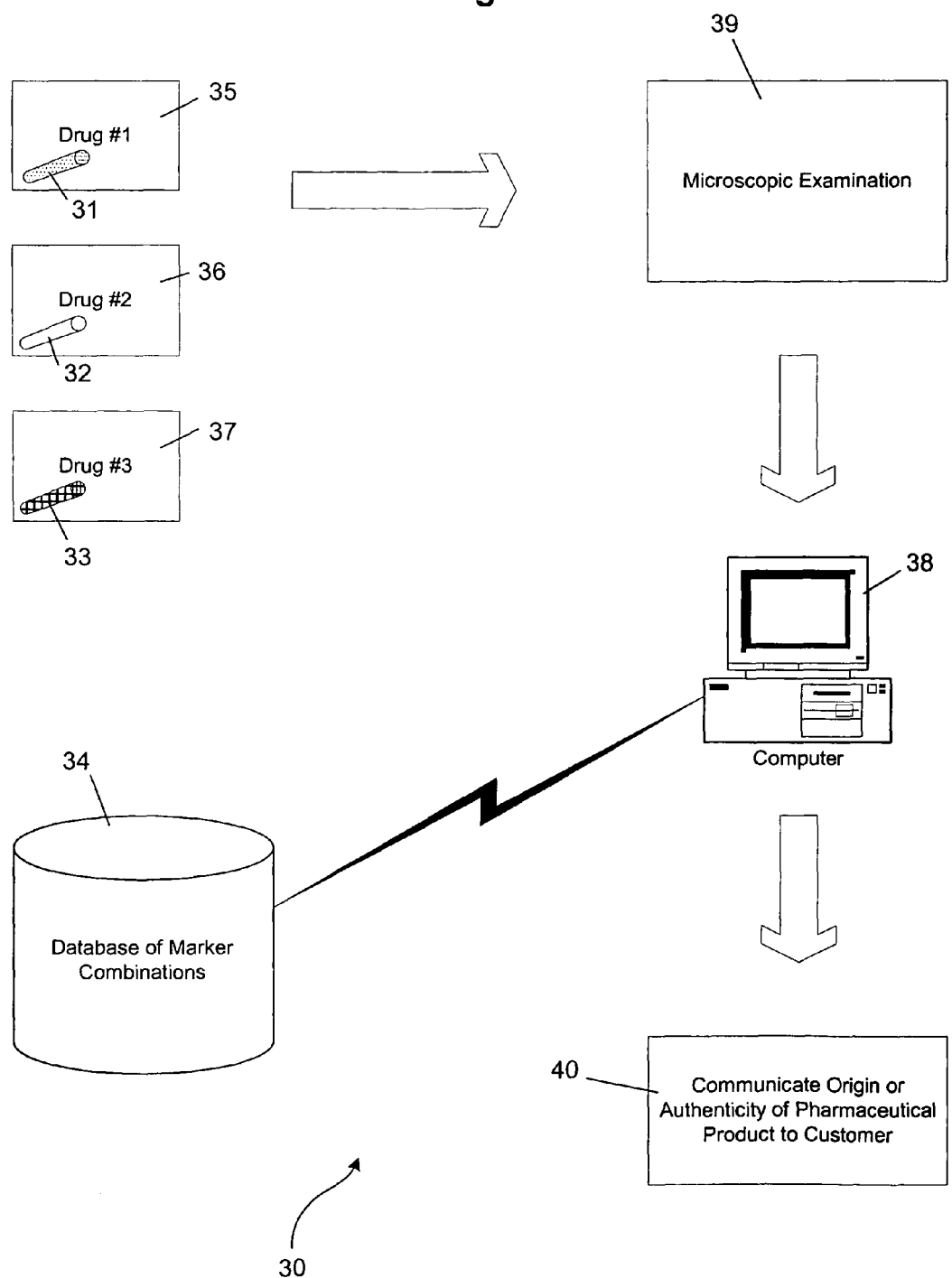
FIG. 3 is a diagram showing a clearinghouse arrangement for tracking and identifying several different marker combinations for pharmaceutical products.

As depicted in FIG. 3, a clearinghouse 30 for keeping track of the several different markers and marker combinations 31, 32, 33 can be provided using the concepts of the present invention. By combining different natural materials and different secondary markers (dyes and reactants), it will be possible to prepare dozens or even hundreds of distinctly different marker combinations that can be rapidly identified using microscopic examination. The clearinghouse 30 will have a database 34 containing a record of the different marker combinations 31, 32, 33 and information about the various pharmaceutical products 35, 36, 37 or other products in which each such marker combination 31, 32, 33 has been used. A simple indexing system using a computer 38 will allow a product examiner at step 39 to match a detected marker combination 31, 32, 33 with a particular pharmaceutical product 35, 36, 37 or product source. The clearinghouse 30 can then offer the valuable service of supplying markers 31-33 to its corporate customers, collecting and storing information about how and where each marker is used, and matching such information with forensic samples of the pharmaceutical products 35-37. The clearinghouse 30 or an independent laboratory can perform the step 39 of examining forensic samples of the pharmaceutical products and using the computer 38 and database 34 to determine the origin or authenticity of the pharmaceutical product samples 35-37. This information can then be communicated to the corporate customer at step 40 and used as necessary to confirm or deny the origin or authenticity of the pharmaceutical product samples 35-37. This clearinghouse arrangement can also be used for tracking markers and marker combinations for non-pharmaceutical products, such as food products, using the concepts of the present invention.

The following table illustrates a progression of eight different marker combinations that can be generated using a single natural cellulosic marker, two colors of dyes (e.g., food coloring), and two colors of chromophores. The dyes and chromophores can be infused into the hollow interior spaces of the natural cellulosic marker material using vacuum infusion or the other techniques described above before adding the marker material to the pharmaceutical product.

TABLE 1

Marker Combinations.

| Company | Natural Marker | Dye | Chromophore |
|---|---|---|---|
| 1 | Hollow Fiber #1 | Red | Brown |
| 2 | Hollow Fiber #1 | Red | Blue |
| 3 | Hollow Fiber #1 | None | Blue |
| 4 | Hollow Fiber #1 | None | Brown |
| 5 | Hollow Fiber #1 | Red | None |
| 6 | Hollow Fiber #1 | Yellow | None |
| 7 | Hollow Fiber #1 | Yellow | Blue |
| 8 | Hollow Fiber #1 | Yellow | Brown |

An additional set of marker combinations can be produced by changing the natural fiber source. For example, a first set of marker combinations can be produced using sycamore seed fibers, and a second set of marker combinations can be produced using oat trichomes. Additional marker combinations can be produced, for example, by using two natural fiber sources in the same product (e.g., sycamore seed fibers and oat trichomes), and/or by using an additional reactant. The additional reactant can be selected so as not to interfere with any of the other reagents used in the detection technique. For example, the additional reactant can be a chromophoric reactant that can be heat activated to change color or pH activated to change color or be an entirely different enzymatic reaction, and so forth.

EXPERIMENTAL EXAMPLES

Several examples of the natural cellulosic plant material markers, secondary markers, molecular thermometers, and methods for preparing the markers have been given above. Specific working examples of the preparation of markers according to the present invention will now be explained.

The unique natural fibers from sycamore seeds were ground to reduce their length. These were blended into a sorbate-propionate food preservative mixture and micro-encapsulated with a fat soluble material. The concentration of marker to product was one part per million in order to verify that very low inclusion rates of markers could be used to confirm identities of products without any significant effects on a finished product. The low inclusion rate preservative was subsequently used to bake bread.

Tiny aliquots (less than 5 milligrams) of the bread were taken for examination. These sample aliquots were further prepared by heating a smaller sub-sample amount of the crumb structure from each sample on a slide in a mounting medium containing chloral hydrate to gelatinize the starch in the crumb structures. The sycamore fiber marker was unaffected by the hot mounting media, and the unique fibers were found in the bread at normal preservative rates. However, the extremely low inclusion rate of the preservative with only one part per million marker slowed the examination and confirmation process.

This experiment proved it was possible to locate unique cellulosic markers at extremely low concentrations in bread. It was possible to find the unique sycamore fiber markers at that concentration, but higher concentrations of markers in the low inclusion rate micro-encapsulated product would make it easier to identify the marked products (bread in this case) and speed up the examination process.

A second experiment to exploit the characteristics of these kinds of tiny hollow markers utilized the markers to prove the concept of making and handling micro-capillary products.

The natural marker material was the hollow cellulosic fibers from milkweed seeds. A small quantity of fibers was ground to reduce their fiber length and make them easier to mix. The fibers were placed in an aqueous red food color dye solution and a gentle vacuum drawn on the container to enhance the transfer of liquid into the micro-capillaries of the milkweed seed fibers. The fibers were subsequently rinsed to remove the excess colored dye and the liquid decanted. The dye in the hollow fibers remained inside the hollow fibers due to capillary forces.

The dye containing hollow fibers were placed in a ferrous salt solution. A gentle vacuum was applied to infuse the ferrous salt into the already dye-marked milkweed seed fibers. The fibers were rinsed to remove the surface absorbed reagent.

These markers were placed in an iron test solution consisting of potassium ferricyanide-potassium ferrocyanide solution (0.5 molar each for each component), and the fibers were examined after the excess iron reagent was rinsed off. The ferrous salt inside the hollow milkweed seed fibers reacted rapidly with the iron reagent to produce a readily seen insoluble indigo blue colored pigment inside the fiber. No iron reactions were observed on the outside of the fibers. This proved all the excess iron salt solution had been removed, and only the interior capillary fixed iron was reacting with the iron reagent. The indigo blue color was readily observed in the micro-capillary milkweed seed fiber tube along with the red food colorant dye. This also proved that multiple components—dyes, reactants, and enzymes—could be vacuum infused sequentially into the natural hollow fibers and then examined. Several mutually exclusive marker components could also be vacuum infused into the hollow fibers at the same time and used to modify the markers for several applications.

A third experiment was conducted to prove that natural marker materials, as described above, are suitable for use in clinical trials to prove that a particular pharmaceutical product or other substance has been ingested.

In this experiment, a small quantity (approximately ⅛ to ¼ teaspoon) of ground, cooked and cooled canola hulls was eaten with each meal for three days. The monitoring protocol was to examine fecal matter adhering to the first wipe of toilet paper for each bowel movement during the testing period. The remainder of the fecal matter was discarded because this experiment was only to confirm the ease of finding markers, to estimate the stool passage time for a particular diet regimen, and to prove that this marker was unaffected by digestion. No attempt was made to measure any markers quantitatively.

The first marker particles passed through the test subject's system in about one and three quarter days and were located with the aid of a hand lens. The marker particles were isolated by manually picking them from the smeared feces on the toilet paper and placing them in a mounting medium on a microscope slide. Some of the marker particles were rinsed in water prior to placing them in the mounting medium, although that was to improve the photographic record and not to aid in the identification of the markers, which were very obvious in the feces.

The markers were isolated at 10-15× magnification under a stereomicroscope. The markers were viewed and photographed with both brightfield and polarized light. The recovered particles were photographed to characterize what changes, if any, had occurred during digestion and how easily the other food particles in the feces could be differentiated from the marker particles.

A small amount of material, primarily oxalate particles and some fibers, was removed from the markers during digestion. It was unknown if some of these particles were actually digested, or if they were removed during passage from rubbing against other particles. The basic test structure of the marker was unchanged. Even an oat trichome (pure cellulose), suggested as a separate marker material, was not digested and could be found easily. Thus, the experiment proved without doubt that the markers remained essentially unchanged and could be located easily under low magnification with a stereomicroscope or lighted lens. It also suggested that the fibers noted above that might have been removed from the markers during passage through the test subject's alimentary tract had not likely been digested, but instead only physically removed from the matrix.

As explained above, the present invention is particularly suitable for marking pharmaceutical products. However, the concepts of the invention can also be used for marking a variety of other manmade products unrelated to the marker materials, including food products, adhesive bandages, medicinal capsules, packaging materials, and various types of cleaning products.

While this invention has been described in relation to the preferred embodiments, it is to be understood that various modifications thereof will now be apparent to one skilled in the art upon reading this specification, and it is intended that all such modifications that fall within the scope of the following claims be covered by this application. The scope of the following claims should be construed as broadly as the prior art will permit.

What is claimed is:

1. A method of proving ingestion of a pharmaceutical product by a person participating in a clinical trial, comprising the steps of:
    selecting a natural material having a unique genetically controlled micromorphological structure that can be identified using microscopic examination;
    adding said natural material to a pharmaceutical product at a sufficiently low level so as not to have any significant effect on the pharmaceutical product other than to serve as a marker for the pharmaceutical product;
    obtaining a stool sample from the person after said pharmaceutical product is allegedly ingested;
    determining by use of microscopic examination whether the stool sample contains said particular natural material by visually identifying said unique genetically controlled micromorphological structure; and
    matching the detected natural material with information about pharmaceutical products that have been marked by natural marker materials to determine the particular pharmaceutical product ingested by the person.

2. The method according to claim 1, wherein said natural material is resistant to visible changes induced by mechanical, physical or chemical processing variables during manufacturing of the pharmaceutical product.

3. A method of proving ingestion of a pharmaceutical product by a person participating in a clinical trial, comprising the steps of:
    selecting a natural material having a unique genetically controlled micromorphological structure that can be identified using microscopic examination;
    adding said natural material to a pharmaceutical product at a sufficiently low level so as not to have any significant effect on the pharmaceutical product other than to serve as a marker for the pharmaceutical product;
    obtaining a stool sample from the person after said pharmaceutical product is allegedly ingested;
    determining by use of microscopic examination whether the stool sample contains said particular natural material by visually identifying said unique genetically controlled micromorphological structure; and
    determining whether said natural material contains a particular visual characteristic indicating the presence of a secondary marker for the marked product.

4. The method according to claim 3, wherein said visual characteristic is a color.

5. The method according to claim 3, wherein said natural material comprises a natural cellulosic plant material, and said visual characteristic is located in a particular structure of said a natural cellulosic plant material.

6. The method according to claim 5, wherein said particular structure is a hollow interior space of the natural material.

7. A method of proving ingestion of a pharmaceutical product by a person participating in a clinical trial, comprising the steps of:
    selecting a natural material having a unique genetically controlled micromorphological structure that can be identified using microscopic examination;
    adding said natural material to a pharmaceutical product at a sufficiently low level so as not to have any significant effect on the pharmaceutical product other than to serve as a marker for the pharmaceutical product;
    obtaining a stool sample from the person after said pharmaceutical product is allegedly ingested; and
    determining by use of microscopic examination whether the stool sample contains said particular natural material by visually identifying said unique genetically controlled micromorphological structure;
    wherein said natural material is selected from the group consisting of cellulosic plant materials and sporopollenin.

* * * * *